United States Patent [19]

Lattrell et al.

[11] 4,141,991
[45] Feb. 27, 1979

[54] FERROCENE DERIVATIVES

[75] Inventors: Rudolf Lattrell; Heinrich Kief, both of Königstein, Taunus; Hermann Bähr, Kelkheim, all of Fed. Rep. of Germany

[73] Assignee: Hoechst Aktiengesellschaft, Frankfurt am Main, Fed. Rep. of Germany

[21] Appl. No.: 799,972

[22] Filed: May 24, 1977

[30] Foreign Application Priority Data

May 26, 1976 [DE] Fed. Rep. of Germany ....... 2623487

[51] Int. Cl.² .................... A01N 9/00; A61K 31/295; A61L 13/00
[52] U.S. Cl. .............................. 424/295; 260/439 CY
[58] Field of Search ................. 424/295; 260/439 CY

[56] References Cited

U.S. PATENT DOCUMENTS

| | | | |
|---|---|---|---|
| 3,432,533 | 3/1969 | Rosenberg | 260/439 CY |
| 3,960,911 | 6/1976 | Suschitzky et al. | 260/439 CY |
| 3,966,783 | 6/1976 | Suschitzky et al. | 260/439 CY |
| 4,036,983 | 7/1977 | Rutherford et al. | 260/439 CY |

FOREIGN PATENT DOCUMENTS

| | | | |
|---|---|---|---|
| 819108 | 5/1959 | United Kingdom | 260/439 CY |
| 864197 | 3/1961 | United Kingdom | 260/439 CY |
| 869504 | 5/1961 | United Kingdom | 260/439 CY |
| 898633 | 6/1962 | United Kingdom | 260/439 CY |

*Primary Examiner*—Helen M. S. Sneed
*Attorney, Agent, or Firm*—Curtis, Morris & Safford

[57] ABSTRACT

Compounds of the formula I

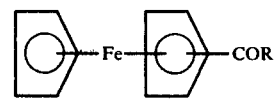

in which R represents a cycloalkenyl radical having 5 to 7 carbon atoms, in which the ethylenic double bond is not in an adjacent position to the CO-group, or a cycloalkenyl radical having 5 to 7 carbon atoms, in which the ethylenic double bond is not in an adjacent position to the CO-group, and substituted one or more times by alkyl having 1 to 4 carbon atoms, phenyl, benzyl or chlorine, process for their manufacture, medicaments containing them and their use for the treatment of sideropenia symptoms and sideropenic anaemiae.

7 Claims, No Drawings

FERROCENE DERIVATIVES

The invention relates to ferrocene derivatives of the formula I

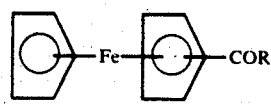

which are distinguished by an extraordinary activity in the treatment of sideropenia symptoms and sideropenic anaemiae.

In the formula, R represents a cycloalkenyl radical having 5 to 7 carbon atoms and in which the ethylenic double bond is not in an adjacent position to the CO-group, or a cycloalkenyl radical having 5 to 7 carbon atoms in which the ethylenic double bond is not in an adjacent position to the CO-group and which is substituted one or more times by alkyl having 1 to 4 carbon atoms, phenyl, benzyl or chlorine.

There come into consideration as preferred radicals R: 2-cyclohexen-1-yl, 3-cyclohexen-1-yl, 2-cyclopenten-1-yl and 3-cyclopenten-1-yl radicals as well as the corresponding radicals substituted by methyl, ethyl, propyl, isopropyl, butyl or tert. butyl.

The following may be mentioned as relevant compounds of the formula I:
4-ferrocenoyl-cyclohexene, 4-ferrocenoyl-4-methyl-cyclohexene, 4-ferrocenoyl-5-methyl-cyclohexene, 4-ferrocenoyl-3,6-dimethyl-cyclohexene, 4-ferrocenoyl-1-methyl-cyclohexene, 4-ferrocenoyl-4-isopropyl-cyclohexene, 4-ferrocenoyl-2-tert.-butyl-cyclohexene, 3-ferrocenoyl-2,4,4-trimethyl-cyclohexene, 3-ferrocenoyl-5-tert.-butyl-cyclohexene, 3-ferrocenoyl-cyclopentene, 3-ferrocenoyl-1-methyl-cyclopentene, 4-ferrocenoyl-cyclopentene, 4-ferrocenoyl-4,5,5-trimethyl-cyclopentene.

The invention also relates to a process for the manufacture of ferrocene derivatives of the formula I, pharmaceutical preparations that contain these or comprise these, and to the use thereof in a, or as a, medicament.

The process for the manufacture of these ferrocene derivatives is characterised in that ferrocene is reacted in an inert solvent, in the presence of a Friedel Crafts catalyst, with an acid halide of the formula R-CO-halogen or an acid anhydride of the formula $(RCO)_2O$.

Processes for the manufacture of acylated ferrocenes are known in principle, wherein diacylated ferrocenes are produced preferably in the presence of aluminium chloride, monoacylated ferrocenes preferably using hydrogen fluoride or polyphosphoric acid (British Patents Nos. 869 504, 819 108). In the preparation of the compounds of formula I according to the invention it was therefore surprising that these can be obtained in a good yield in the form of monoacylferrocene derivatives also when using aluminium chloride. In comparison with hydrogen fluoride, the use of aluminium chloride has the advantage that it is not dangerous to handle and is simpler to meter in.

A preferred process for the preparation of the compounds I consists in reacting ferrocene with acid chlorides RCOCl or acid anhydrides $(RCO)_2O$ in inert solvents, such as, methylene dichloride, ethylene dichloride or carbon disulphide, in the presence of aluminium trichloride. The acid derivative is used in a quantity at least equimolar to the ferrocene up to a 10% excess, the aluminium chloride in a quantity that corresponds to the quantity of acid derivative used. The reaction is carried out between $-30°$ and $60°$ C., preferably between $-10°$ and $20°$ C.

The process according to the invention is preferably carried out with the acid chloride in the presence of aluminium chloride and methylene chloride as solvent.

In the preferred method of carrying out the process, either the acid chloride can be added dropwise to the ferrocene and aluminium chloride in methylene chloride, or it is possible to add to the suspension of aluminium chloride in methylene chloride, a mixture of ferrocene and acid chloride, dissolved in methylene chloride. A particularly pure product is obtained in a good yield if a mixture of acid chloride and aluminium chloride in methylene chloride is added to the solution of ferrocene in methylene chloride, or if aluminium chloride is added in portions to a solution of ferrocene and acid chloride in methylene chloride.

The compounds according to the invention are suitable for treating sideropenia symptoms and sideropenic anaemiae.

After oral administration, sideropenia resulting from by-passing the normal regulating mechanism in the intestine for ionic iron, is quickly compensated. Thus, the results of an iron-deficient diet for rats and mice, such as reduced body weight, decrease of hemoglobin, of the hematocrit, of the serum iron and of the number of erythrocytes, is fully compensated by the administration once of a dose of one of the compounds according to the invention corresponding to 2 mg of iron per animal. The compounds according to the invention are resorbed well orally, the excretion of unchanged substance in urine usually being less than 1%. The compounds are distinguished by a distinct nontoxicity, the $LD_{50}$ of 4-ferrocenoyl-cyclohexene thus amounting to 2000 mg/kg in mice and 3,000 mg/kg in rats. As can be shown by biochemical determination of the ferritin protein and its degree of iron saturation, the compounds are completely metabolised in the liver, that is, the iron is released and incorporated in the storage form that can be used to form hemoglobin, that is in liver ferritin, and in the case of an excess of added substance, in ferritin and in hemosiderin. These discoveries are supported by histological comparison tests, in which the increase of liver ferritin is recognisable in a Berlin-blue reaction in the form of a uniform blue shading of the cytoplasma of the liver cells, and any hemosiderin that may have formed is recognisable in the form of fine blue grains.

The compounds are clearly superior to known ferrocene derivates in their capability to increase the iron of the liver that can be used to form blood. This is shown by comparative tests of 4-ferrocenoylcyclohexene

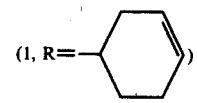

with the ferrocene derivatives 2a–d described in British Patents Nos. 819 108 and 869 504, wherein 2d is, according to details in the literature (Brit. J. Pharmacol, 24, 352, 1965) the best, especially regarding its ability to utilize the iron.

(2a) hexahydrobenzoyl ferrocene
(2b) 1,1'-di-(3,5,5-trimethyl-hexanoyl)-ferrocene (2c) 1,1'-di-hexahydrobenzoyl ferrocene
(2d) 1,1'-di-neopentyl ferrocene The compounds were administered to 6 male rats and 6 male mice on two successive days in individual doses corresponding to an iron content of 52.2 mg Fe per kg of animal. 24 hours after the 2nd administration the animals were killed. Histologically, the compound according to the invention

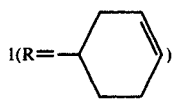

in comparison with 2a and 2b exhibits a substantially greater increase of the liver ferritin, and in addition individual hemosiderin particles are observed. 2c and 2d do not cause any histologically recognisable increase of the liver ferritin. The quantitative determination of the ferritin protein and its iron content (table) confirm these findings. For this, ferritin is isolated from the liver by thermal denaturation, ammonium sulfate fractionation and gel filtration, and the protein is determined by amino acid analysis and the iron content by atom absorption.

TABLE

| | Analysis of the ferritin from rat livers[1] | | | |
|---|---|---|---|---|
| Substance | Ferritin-iron μg/g tissue | Ferritin-protein μg/g tissue | Ratio of iron to protein | Dosage[2] mg/kg |
| 1 | 1133 | 950 | 1.19 | 2 × 275 |
| 2 a | 209 | 475 | 0.43 | 2 × 277 |
| 2 b | 148 | 567 | 0.26 | 2 × 436 |
| 2 c | 94 | 224 | 0.42 | 2 × 380 |
| 2 d | 61 | 130 | 0.38 | 2 × 380 |
| Control | 59 | 365 | 0.16 | — |

[1]Average values from 6 animals
[2]Corresponds to 52.5 mg Fe/kg of animal

It is evident from the table that after administration of the compound

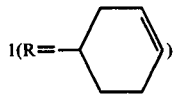

according to the invention in comparison with the known compounds 2a–d, the ferritin protein and its iron content has clearly increased more markedly.

The compounds according to the invention are used as active components in pharmaceutical preparations, preparations for oral administration being preferred. The preparations may contain the active substance per se or in admixture with other substances. The level of the dose administered obviously depends on the type of treatment desired and on the method of administration. In the case of oral administration satisfactory results are obtained with doses of 10 to 300 mg of active substance per kg of animal body weight; in the case of man the daily dosage varies between 50 and 1000 mg of active substance per person, wherein individual doses of 50 to 1000 mg, in particular 50 to 250 mg, may be administered preferably once to three times daily.

The forms of preparation that come into consideration for oral administration are, for example, tablets, push-fit capsules, alcoholic or oily suspensions or solutions. Suitable inert carriers for tablets and dragees are, for example, magnesium carbonate, lactose, stearic acid, milk sugar or maize starch, with the addition of other substances such as, for example, magnesium stearate. The preparation in this case may occur either as a dry or moist granulate. The oily carrier substances or solvents considered are especially vegetable, animal or synthetic oils, such as cod liver oil or sunflower oil.

The active compounds can also be made up into a paste, chewing gum, tablets that are to be chewed, or a drink ampoule or may be combined with foodstuffs. The preparations may also contain other pharmacologically active components, such as vitamins, for example, vitamin $B_{12}$, vitamin C or folic acid, analgesic agents such as acetylsalicyclic acid or anthelmintic agents. The preparations may further contain, as additions, preservatives and stabilizers, sweeteners or flavouring substances. A suitable form of preparation for oral administration is, for example, gelatin capsules that contain a solution of 137 mg of 4-ferrocenoyl-cyclohexene dissolved in Mygliol.

The invention is explained by the following Examples.

EXAMPLE 1

4-Ferrocenoyl-cyclohexene

A mixture of 140 g (0.75 mole) of ferrocene and 120 g (0.83 mole) of 3-cyclohexen-1-carboxylic acid chloride in 2.2 l of methylene chloride is cooled to −10° C. and then, at −10° to −5° C. 107 g (0.8 mole) of aluminium trichloride is added in portions over a period of 45 minutes. Stirring is carried out for 3 hours at −5° C., then, after the addition of 2 l of ice water, stirring is carried out for 15 minutes. The organic phase is separated off and washed in succession with water, saturated, aqueous sodium bicarbonate solution and again with water. The solvent is removed in vacuo and the oily residue is dissolved in 500 ml of petroleum ether (40° to 80° C.). A crystal sludge is precipitated out by triturating, which is suction-filtered after standing overnight. After washing twice with petroleum ether, 161 g of red crystalline product having a melting point of 75° to 76° C. is obtained.

A further 31 g are isolated from the mother liquor by chromatography over silica gel with toluene (RF value = 0.3).

EXAMPLE 2

3-Ferrocenoyl-1-methyl-cyclohexene

Prepared from ferrocene, 3-methyl-2-cyclohexen-1-carboxylic acid chloride and aluminium chloride in methylene chloride at 0° C. in a manner analogous to that described in Example 1.

The compound is obtained in an 82% yield in the form of a red oil.

EXAMPLE 3

4-Ferrocenoyl-4-isopropyl-cyclohexene

Prepared from ferrocene, 1-isopropyl-3-cyclohexene-1-carboxylic acid chloride and aluminium chloride in methylene chloride at 0° C. in a manner analogous to that described in Example 1.

A red-coloured oil is obtained in a yield that is 55% of the theoretical yield.

EXAMPLE 4

4-Ferrocenoyl-2,3,3-trimethyl-cyclopentene

Prepared from ferrocene, 2,2,3-trimethyl-3-cyclopenten-1-carboxylic acid chloride and aluminium chloride in methylene chloride at 0° C. in a manner analogous to that described in Example 1.

A dark-red-coloured oil is obtained in a yield that is 72% of the theoretical yield.

We claim:

1. Compounds of the formula I

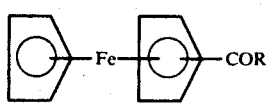

I in which R represents a cycloalkenyl radical having 5 to 7 carbon atoms in which the ethylenic double bond is not in an adjacent position to the CO-group, or a cycloalkenyl radical having 5 to 7 carbon atoms in which the ethylenic double bond is not in an adjacent position to the CO-group and which is substituted one or more times by alkyl having 1 to 4 carbon atoms, phenyl, benzyl or chlorine.

2. Compounds as claimed in claim 1, in which R represents a 2-cyclohexen-1-yl radical which may be substituted by $C_2$ to $C_4$-alkyl, phenyl, benzyl or chlorine.

3. Compounds as claimed in claim 1, in which R represents a 3-cyclohexen-1-yl radical, which may be substituted by $C_1$ to $C_4$-alkyl, phenyl, benzyl or chlorine.

4. Compounds as claimed in claim 1, in which R represents a 2-cyclopenten-1-yl radical, which may be substituted by $C_1$ to $C_4$-alkyl, phenyl, benzyl or chlorine.

5. Compounds as claimed in claim 1, in which R represents a 3-cyclopenten-1-yl radical, which may be substituted by $C_1$ to $C_4$-alkyl, phenyl, benzyl or chlorine.

6. A medicament useful in the oral treatment of sideropenia symptoms and sideropenic anaemiae containing an effective amount of a ferrocene derivative according to claim 1 and a pharmaceutically acceptable carrier.

7. A method for the treatment of sideropenia symptoms and sideropenic anaemiae in a patient requiring such treatment which comprises administering orally to said patient an effective amount of a compound as claimed in claim 1.

* * * * *